US 10,512,685 B2

United States Patent
Vermeij et al.

(10) Patent No.: US 10,512,685 B2
(45) Date of Patent: Dec. 24, 2019

(54) HEV VACCINE

(71) Applicant: Intervet Inc., Madison, NJ (US)

(72) Inventors: Paul Vermeij, St. Anthonis (NL); Ad Groof De, Groesbeek (NL); Carla Christina Schrier, Boxmeer (NL); Wannes Vogels, Nijmegen (NL)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 16/302,891

(22) PCT Filed: May 24, 2017

(86) PCT No.: PCT/EP2017/062638
§ 371 (c)(1),
(2) Date: Nov. 19, 2018

(87) PCT Pub. No.: WO2017/202973
PCT Pub. Date: Nov. 30, 2017

(65) Prior Publication Data
US 2019/0151442 A1    May 23, 2019

(30) Foreign Application Priority Data

May 25, 2016 (EP) .................................. 16171324

(51) Int. Cl.
| | | |
|---|---|---|
| C07K 14/005 | (2006.01) | |
| C07K 14/08 | (2006.01) | |
| A61K 39/00 | (2006.01) | |
| A61K 39/29 | (2006.01) | |
| C12Q 1/70 | (2006.01) | |
| A61K 39/12 | (2006.01) | |
| A61P 31/14 | (2006.01) | |
| A61K 39/39 | (2006.01) | |

(52) U.S. Cl.
CPC .............. *A61K 39/29* (2013.01); *A61K 39/12* (2013.01); *A61K 39/39* (2013.01); *A61P 31/14* (2018.01); *A61K 2039/545* (2013.01); *A61K 2039/552* (2013.01); *A61K 2039/555* (2013.01); *C12N 2770/28034* (2013.01)

(58) Field of Classification Search
CPC ........ C07K 14/005; C12N 2770/28122; C12N 7/00; A61K 39/00; A61K 38/00
See application file for complete search history.

(56) References Cited

FOREIGN PATENT DOCUMENTS

| EP | 1000168 B1 | 11/2006 |
| WO | WO02/089733 A | 11/2002 |

OTHER PUBLICATIONS

Ahmad, I. et al., Molecular Virology of Hepatitis E Virus, Virus Res., 2011, pp. 47-58, 161(1).
Amini-Bavil-Olyaee, S. et al., Hepatitis E vaccine: current status and future propects, Future Virology, 2009, pp. 143-154, 4(2).
Andraud, M. et al., Early-life Hepatitis E Infection in Pigs: The Importance of Maternally-Derived Antibodies, PLOS ONE, Aug. 2014, pp. e105527, vol. 9, Issue 8.
Barnaud et al, Thermal Inactivation of Infectious Hepatitis E Virus in Experimentally Contaminated Food, Applied and Environmental Microbiology, Aug. 1, 2012, pp. 5153-5159, vol. 78, No. 15.
De Deus et al, Hepatitis E Virus Infection Dynamics and Organic Distribution in Naturally Infected Pigs in a Farrow Ti Finish Farm, Veterinary Microbiology, Nov. 25, 2008, 19-28, vol. 132, No. 1-2, Elsevier.
Extended European Search Report for 16171324.3 dated Oct. 27, 2016, 3 Pages.
Huang et al, Effective Inhibition of Hepatitis E Virus Replication in A549 Cells and Piglets by RNA Interference (RNAi) Targeting RNA-Dependent RNA Polymerase, Antiviral Research, Sep. 1, 2009, pp. 274-281, vol. 83, No. 3, Elsevier.
International Search report and written opinion for PCT/EP2017/062638 dated Jul. 28, 2017, 21 pages.
Kawczynski et al, Pathogenic Elements of Hepatitis E and Animal Models of HEV Infection, Virus Research, 2011, pp. 78-83, vol. 161, No. 1.
Li, Tian-Cheng et al., Essential Elements of the Capsid Protein for Self-Assembly into Empty Virus-Like Particles of Hepatitis E Virus, Journal of Virology, 2005, pp. 12999-13006, vol. 79, No. 20.
Lu, Ling et al., Phylogenetic analysis of global hepatitis E virus sequences: genetic diversity, subtypes and zoonosis, Rev. Med. Virol., 2006, pp. 5-36, 16.
Meng, Xiang-Jin et al., A novel virus in swine is closely related to the human hepatitis E virus, Proc. Natl. Acad. Sci. USA, Sep. 1997, pp. 9860-9865, vol. 94.
Nieuwiesk, S., Maternal antibodies: clinical significance, mechanism of interference with immune responses, and possible vaccination strategies, Frontiers in Immunology, Immunotherapies and Vaccines, Sep. 2014, pp. 1-15, vol. 5, Article 446.
Pastoret, P.-P., Challenges and Issues of Early Life Vaccination in Animals and Humans, J. Comp. Path., 2007, pp. S2-S3, vol. 137.
Purcell, R.H. et al, Hidden danger: the raw facts about hepatitis E virus, J. Infect. Dis., 2010, pp. 819-821, 202 (6).
Kamili et al, Toward the Development of a Hepatitis E Vaccine, Virus Research, 2011, pp. 93-100, vol. 161, No. 1.
Surjit, M. et al., The ORF2 Protein of Hepatitis E Virus Binds the 5' Region of Viral RNA, Journal of Virology, 2004, pp. 320-328, vol. 78, No. 1.
Vasickova, P. et al., Hepatitis E virus: a review, Veterinami Medicina, 2007, pp. 365-384, 52(9).
XP002763518.
Zhu, Feng-Cai et al., Efficacy and safety of a recombinant hepatitis E vaccine in healthy adults: a large-scale, randomised, double-blind placebo-controlled, phase 3 trial, The Lancet, 2010, pp. 895-902, vol. 376, Issue 9744.

*Primary Examiner* — Barry A Chestnut

(57) ABSTRACT

The present invention relates to a vaccine comprising Open Reading Frame 2 (ORF2) protein of Swine Hepatitis E virus (HEV) and a pharmaceutically acceptable carrier, for use in the protection of anti-HEV MDA-positive piglets against HEV fecal shedding.

Figures 1A, 1B:
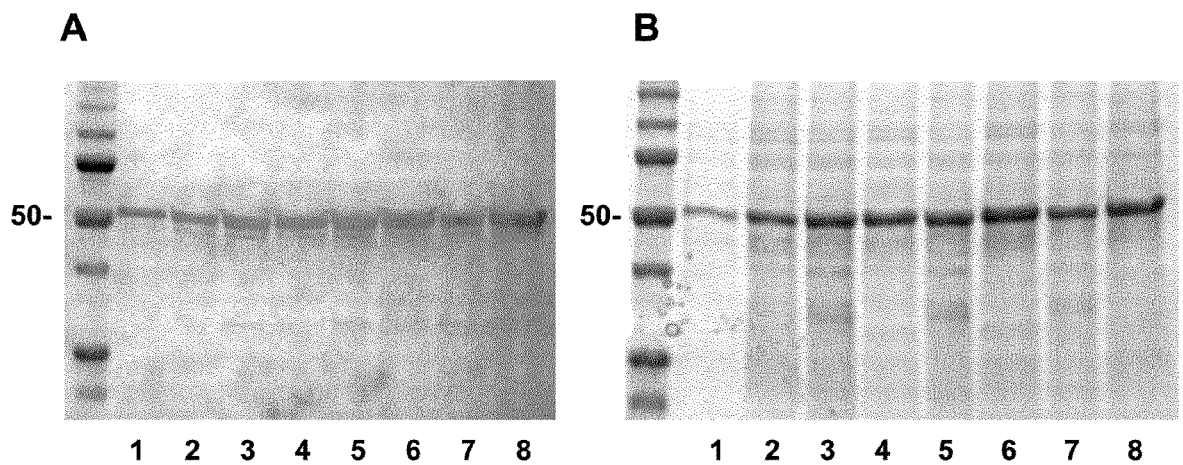

9 Claims, 6 Drawing Sheets
Specification includes a Sequence Listing.

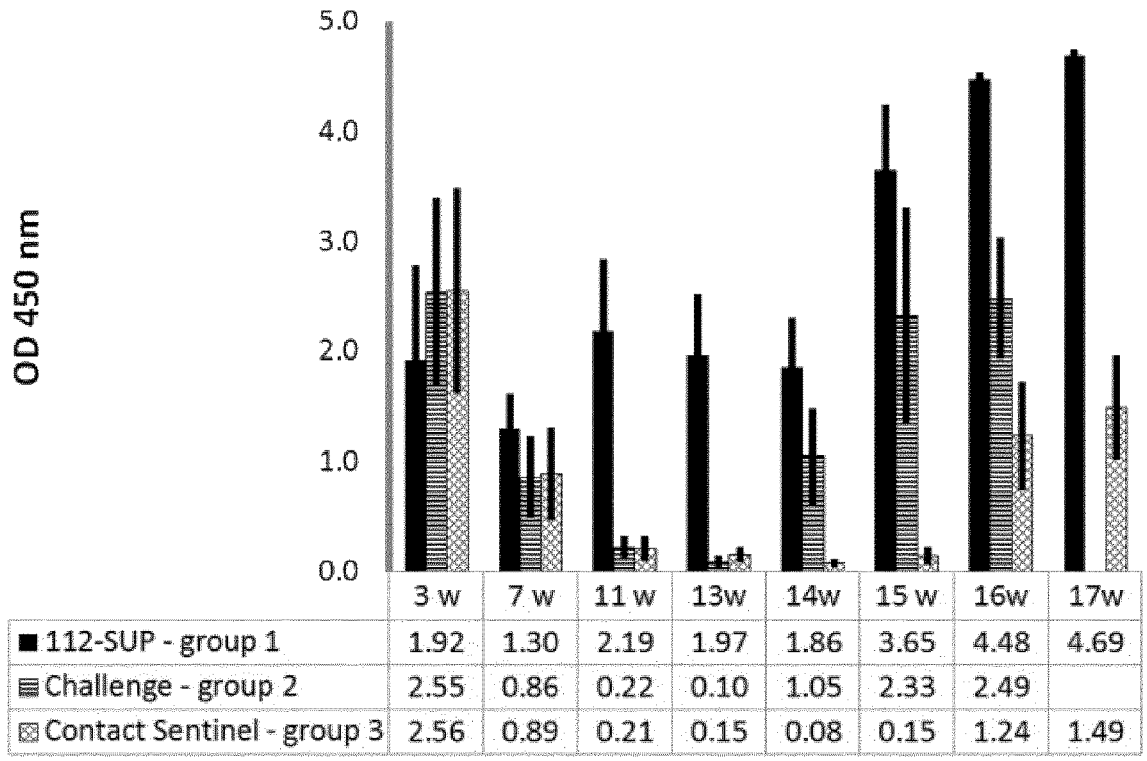

Figure 4.

MAVSPAPDTAPVPDVDSRGAILRRQYNLSTSPLTSSVASGTNLVLYAAPLNPLLPLQDGTNTH
IMATEASNYAQYRVVRATIRYRPLVPNAVGGYAISISFWPQTTTTPTSVDMNSITSTDVRILVQ
PGIASELVIPSERLHYRNQGWRSVETSGVAEEEATSGSVMLCIHGSPVNSYTNTPYTGALGLL
DFALELEFRNLTPGNTNTRVSRYTSTARHRLRRGADGTAELTTTAATRFMKDLHFTGTNGVG
EVGRGIALTLFNLADTLLGGLPTELISSAGGQLFYSRPVVSANGEPTVKLYTSVENAQQDKGI
AIPHDIDLGDSRVVIQDYDNQHEQDRPTPSPAPSRPFSVLRANDVLWLSLTAAEYDQTTYGSS
TNPMYVSDTVTFVNVATGAQAVARSLDWSKVTLDGRPLTTIQQYSKTFYVLPLRGKLSFWE
AGTTKAGYPYNYNTTASDQILIENAAGHRVAISTYTTSLGAGPVSVSAVGVLAPHSALHHHH
HH

Figure 5.

ATGGCTGTTTCTCCCGCTCCCGACACTGCTCCCGTTCCCGACGTGGACTCTCGTGGTGCCA
TCCTGCGTCGTCAATACAACCTTTCTACCTCACCCCTGACTAGCTCTGTTGCTAGCGGAAC
CAACCTGGTGCTTTACGCTGCTCCCCTGAACCCCCTGCTTCCCCTTCAAGACGGCACTAAC
ACCCACATCATGGCCACCGAGGCTAGCAACTACGCCCAATACCGTGTTGTGCGTGCTACC
ATCCGTTACCGTCCCTGGTTCCCAACGCTGTGGGCGGTTACGCTATCAGCATCTCTTTCT
GGCCCCAAACCACTACCACTCCCACCAGCGTTGACATGAACTCTATCACTTCAACCGACG
TTCGTATCCTGGTGCAACCCGGCATCGCTAGCGAACTCGTTATCCCCTCTGAGCGTCTGCA
CTACCGTAACCAAGGCTGGCGTAGCGTTGAAACCTCTGGTGTGGCCGAGGAAGAGGCTA
CTTCAGGAAGCGTTATGCTGTGCATCCATGGCTCACCCGTGAACAGCTACACTAACACCC
CCTACACCGGAGCTCTGGGTCTCCTGGACTTCGCTCTCGAACTGGAGTTCCGTAACCTTAC
CCCCGGCAACACTAACACCCGTGTTTCTCGTTACACTTCAACCGCTCGTCACCGTCTTCGT
CGTGGAGCCGACGGAACCGCTGAACTCACCACTACCGCTGCCACTCGTTTCATGAAAGAC
CTGCATTTCACTGGCACCAACGGCGTTGGCGAAGTGGGACGTGGCATCGCCCTTACTCTC
TTCAACCTTGCTGACACCCTTCTCGGAGGCCTCCCCACTGAACTGATCTCAAGCGCTGGTG
GACAACTCTTCTACTCACGTCCCGTTGTGAGCGCTAACGGCGAACCCACTGTTAAACTGT
ACACCAGCGTGGAGAACGCCCAACAAGACAAGGGTATCGCTATCCCCCACGACATCGAC
CTTGGAGACTCTCGTGTTGTGATCCAAGACTACGACAACCAACATGAGCAAGACCGTCCC
ACCCCCAGCCCCGCTCCCTCTCGTCCCTTCTCAGTTCTGCGTGCTAACGACGTGCTGTGGC
TTAGCCTCACCGCTGCCGAATACGACCAAACTACCTACGGCTCTTCAACTAACCCCATGT
ACGTTAGCGACACTGTGACCTTCGTTAACGTGGCTACCGGCGCTCAAGCCGTTGCTCGTA
GCCTCGACTGGTCTAAGGTGACCCTTGACGGTCGTCCCCTCACTACCATCCAACAATACTC
TAAGACCTTCTACGTTCTGCCCCTTCGTGGTAAACTGTCATTCTGGGAGGCCGGTACTACC
AAGGCTGGATACCCCTACAACTACAACACTACCGCTAGCGACCAAATCCTTATCGAAAAC
GCTGCCGGCCATCGTGTTGCTATCTCTACCTACACTACCTCACTCGGTGCTGGACCCGTGA
GCGTGTCAGCCGTTGGCGTGCTTGCTCCCCACTCTGCCCTCCATCATCATCACCATCATTA
A

Figure 6.

HEV VACCINE

CROSS-REFERENCE TO RELATED APPLICATIONS

This application is a national stage entry under 35 U.S.C. § 371 of PCT/EP2017/062638 filed on May 24, 2017, which claims priority to EP16171324.3 filed on May 25, 2016, the contents of which are hereby incorporated by reference in their entireties.

The present invention relates to a vaccine comprising Open Reading Frame 2 (ORF2) protein of Swine Hepatitis E virus (HEV) and a pharmaceutically acceptable carrier, for use in the protection of MDA-positive piglets against Swine HEV shedding.

Over the last decade a strong increase of human Hepatitis E infection is seen worldwide. Currently, about 20 million HEV infections are reported on a yearly basis, over three million acute cases of hepatitis and 57.000 HEV-related deaths are seen.

Hepatitis E virus, the causative agent of hepatitis E belongs to the genus Hepevirus, the only member of the Hepeviridae. It is a non-enveloped virus with a diameter of about 27-34 nm. The genome, a positive sense single-stranded RNA genome, has a length of about 7.2 kb.

The genome comprises three different open reading frames (ORFs); ORF1, encoding a non-structural protein, ORF2, encoding the viral capsid polypeptide and ORF3 encoding a small phosphoprotein that associates with the cytoskeleton.

Only a single serotype exists. Nevertheless, given the high level of genomic diversity between the various isolates, a sub-division is made into four major genotypes (genotypes 1-4).

HEV is the main cause of non-A, non-B hepatitis in humans. Major outbreaks are found in the developing countries, especially in the tropics and subtropics. In the industrialised countries, HEV infections are seen in regions where HEV is not endemic, even in cases where the patients could not be linked to HEV infected individuals.

HEV genotype 1 and 2 infection is most frequently seen in individuals between 15 and 35 years of age. HEV genotype 3 and 4 infection is more frequently seen in immunocompromised and immune deficient humans, and in organ transplant recipients. It seems that most HEV 3 and 4 infections in healthy people are subclinical. (Ling Lu et al., Rev. Med. Virol. 16: 5-36 (2006)).

Vaccines against human HEV infection have been under development for many years already. In most cases, such vaccines are based upon the HEV ORF 2 protein or fragments thereof, expressed in e.g. baculovirus expression systems and bacterial expression systems. Such vaccines are reported to be successful. (Kamili, S., Virus Research 161: 93-100 (2011), Amini-Bavil-Olyaee, S. et al., Future Virol. 4: 143-154 (2009), Feng-Cai Zhu et al., The Lancet, Published Online Aug. 23, 2010 DOI:10.1016/50140-6736(10) 61030-6.)

It is now commonly accepted that there is a zoonotic relation between (at least) swine HEV genotype 3 and 4 and human disease.

Especially swine are a main reservoir for HEV genotype 3 and 4. (Pavio, N. et al., Curr. Opin. In Virology 10: 34-41 (2015), Purcell, R. H. and Emerson, S. U., J. Inf. Dis. 202: 819-821 (2010), Meng, X. J. et al., P.N.A.S. 94: 9860-9865 (1997), WU, J. C. et al., J. Med. Virol. 60: 166-171 (2000), Matsuda, H. et al., J. Inf. Dis. 188, 944 (2003), Matsubayashi, K. et al., Transfusion 48: 1368-1375 (2008), Mishiro, S., Uirusu 54: 243-248 (2004), Dalton, H. R. et al., Lancet Inf. Dis. 8: 698-709 (2008)).

Infection of humans with HEV genotype 3 and 4 infection is in most of the cases caused by contaminated food, (e.g. undercooked or raw pig meat), direct exposure to swine and swine feces or environmental contamination.

Given this clear illustration of the zoonotic character of HEV, it would seem useful to vaccinate pigs (in addition to humans, or even instead of humans) against swine HEV, in order to avoid swine HEV as a source of human infection.

A few patent applications exist that relate to Swine Hepatitis E virus ORF2 protein and its use in virus detection and as a vaccine. PCT application WO 02/089733 and European patent application EP1000168 basically aim at vaccinating humans against swine HEV using swine HEV whole virus or swine HEV-based subunit vaccines. EP1000168 suggests using swine HEV as a live attenuated virus for vaccination of humans. Swine vaccination is mainly suggested as a means for obtaining anti-swine HEV antibodies for diagnostic purposes, i.a. to check if pig organs for use in xenotransplantation are free of HEV. It is disclosed how, for the purpose of obtaining anti-swine HEV antibodies, Specified Pathogen Free piglets of 2 weeks of age are infected with swine HEV in order to raise antibodies against that infection. Such piglets are i.a. free of maternally derived anti-HEV antibodies. However, these patent applications do not present any examples of swine vaccination, let alone that they address the age of the animal to be vaccinated.

In general, it may seem attractive to vaccinate animals against a disease as soon as possible after their birth. In practice however, and especially in the case of HEV, the skilled person would not consider this to be a suitable approach.

The reason is the following: the prevalence of anti-HEV antibodies in pigs is extremely high. Worldwide, the overall average prevalence is estimated to be 50% (Vasickova, P, et al., Veterinarni Medicina 52: 365-384 (2007)), but it can be significantly higher in many countries. E.g. in 2013, the prevalence of anti-HEV antibodies in pigs in the UK was found to be 92.8% (Grierson, S., et al, CDC EID Journal 21 number 8, August 2005). It can thus be concluded that by far most pig-farms are HEV-infected, and that infection pressure is very high.

As a consequence, by far most of the pigs will have experienced HEV-infection and will have developed anti-HEV antibodies by the time of their first pregnancy. This in turn means that by far most of the piglets born will have maternally derived antibodies (MDAs) against HEV, i.e. most of the piglets born are anti-HEV MDA positive. These maternally derived antibodies will protect the piglets during the first months of their life. Thereafter the MDAs will slowly disappear so, due to the high infection pressure, at a certain moment in time the piglets are susceptible and consequently will experience a HEV infection and consequently may start shedding HEV-virus into the environment before building up their own defense against HEV, i.a. in the form of anti-HEV antibodies.

As a consequence, the HEV-infection pressure in pig farms will stay high.

In the pig farming industry, pigs are weaned between 3 and 4 weeks after birth. This means that they have very high MDA titers at three or four weeks of age. Thereafter a slow decay of the MDA titer is seen.

On the average, if weaning is done at 3 weeks after birth, usually at the earliest after about 7 to 13 weeks an increase is seen in the number of piglets that become infected with HEV and develop their own immune reaction towards this HEV infection. It frequently takes between 10 and 25 weeks before the MDA in piglets is decreased to the level that does not prevent HEV infection in 90% of the animals (See, Example section Ex. 3 and i.a. Andraud, M. et al., PLOS one 9: e105527 (2014)). Before this 10-25 weeks period the MDAs protect a certain percentage of the animals against infection, because the MDAs bind to the virus and remove it before it can infect cells and trigger the immune system.

As a consequence, the skilled person would assume that vaccination of a herd of piglets before 10-25 weeks would in a high percentage of the piglets have no effect for the simple reason that many piglets in the herd would still have sufficiently high MDA titers to interfere with the immunogenic components of a HEV vaccine before it could trigger the immune system. Inhibition of vaccination by MDA's is a common phenomenon, both for human as well as veterinary vaccines (Stefan Niewiesk in Frontiers in Immunology, review article, 16 Sep. 2014; doi:10.3389/fimmu.2014.00446). Thus, vaccination in this period would not be considered useful for these piglets. However, on the other hand, those piglets in the herd that already have a decreased MDA-level are susceptible to HEV-infection and should thus be vaccinated.

It is practically/economically impossible to determine the MDA level in every individual piglet on a daily basis and to decide on a daily basis which individual piglets must be vaccinated.

This long but variable life span of MDAs against HEV is a well-known phenomenon, and from a point of view of vaccination it is a well-known problem. This problem exists not only for MDAs against HEV, it is a problem for vaccination at young age in general. (Andraud, M. (vide supra), Niewiesk, S., Frontiers in Immunology 5, Article 446 (2014), Pastoret, P. P., Journal of Comparative Pathology Volume 137, Supplement 1, Pages S2-S3 (2007)).

Andraud, M. (vide supra) describes the issue of MDAs and the problem as follows: "Although vaccination could overcome this issue (risk of infection during waning of MDAs) several studies evidenced antagonistic effects between vaccine-induced immunity and maternally derived antibodies through inhibition of vaccine protection, which could potentially worsen the dynamics of infection". Niewiesk, S., (vide supra) even describes for 11 different human vaccines and 17 different veterinary vaccines that they are inhibited by maternally derived antibodies.

It is an objective of the present invention to overcome the problem of the presence of MDAs when vaccinating piglets against HEV.

It was now surprisingly found, that a vaccine comprising an immunogenically effective amount of a fragment of HEV ORF2 protein spanning at least the region from amino acid 125 to 607 to at most the region from amino acid 112 to 660 is capable of breaking through the maternal immunity and triggering the immune system of ant-HEV MDA-positive piglets, in particular anti-HEV MDA positive piglets before 10 weeks of age.

In FIG. 3, a comparison is made between the anti-HEV immune response in 3-week old MDA-positive piglets (FIG. 3C) and in 10-week old MDA-negative piglets (FIG. 3D), measured at four weeks after vaccination with a HEV ORF2 fragment according to the invention.

As follows from the figure, surprisingly the anti-HEV titer induced in MDA-positive piglets at four weeks after vaccination is statistically similar to the anti-HEV titer in MDA-negative piglets at four weeks after vaccination.

Figure 3A:
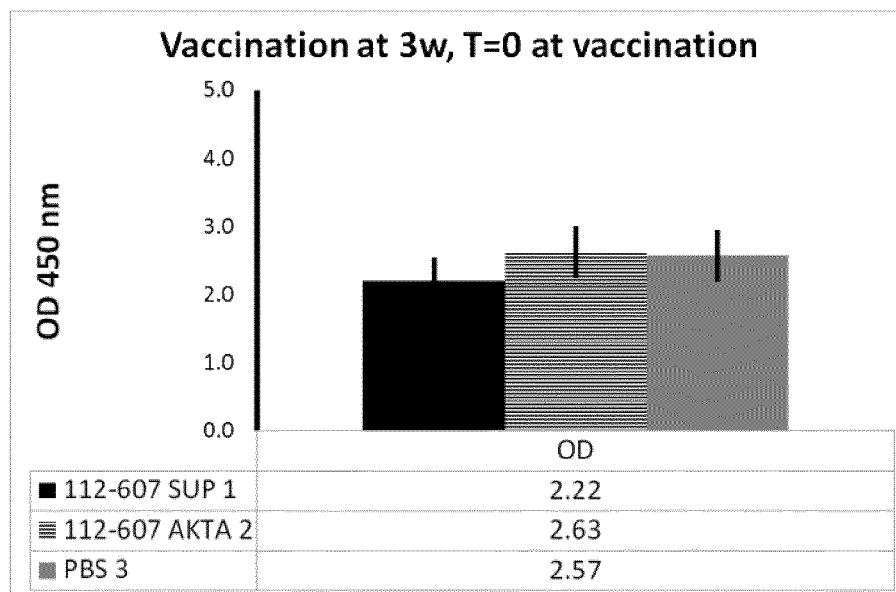
Figure 3B:
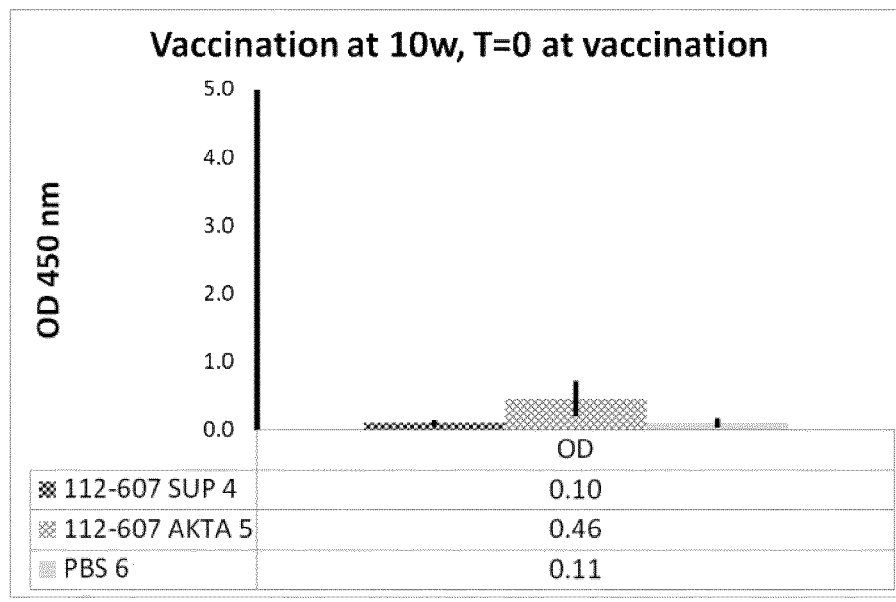
Figure 3C:
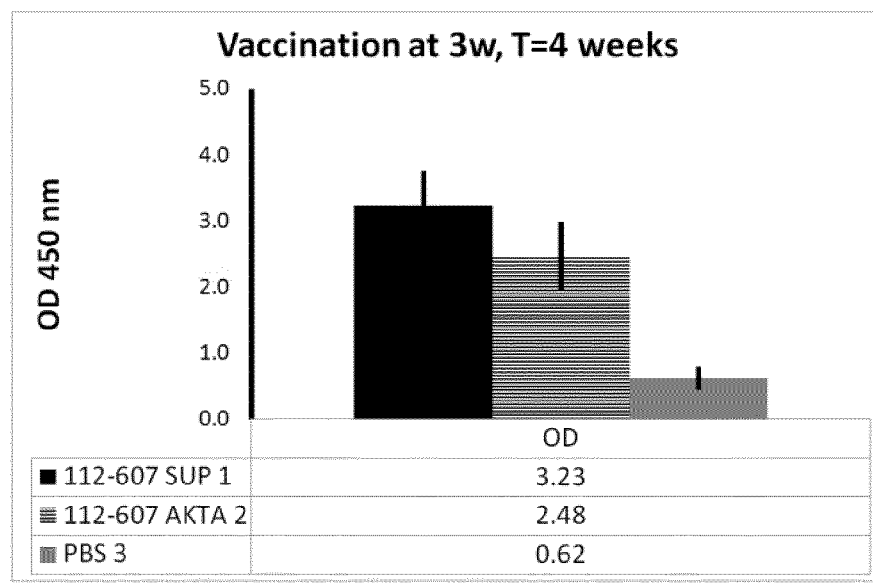
Figure 3D:
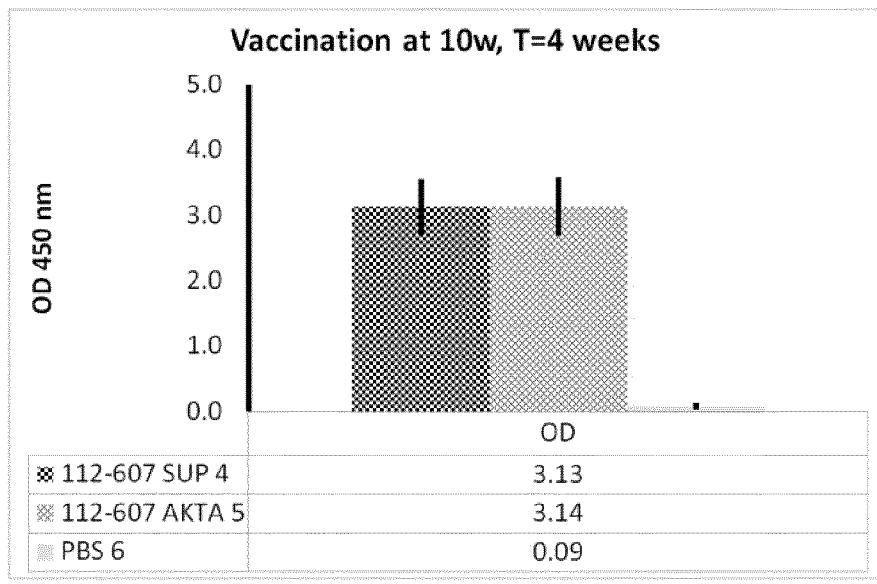
Figure 3E:
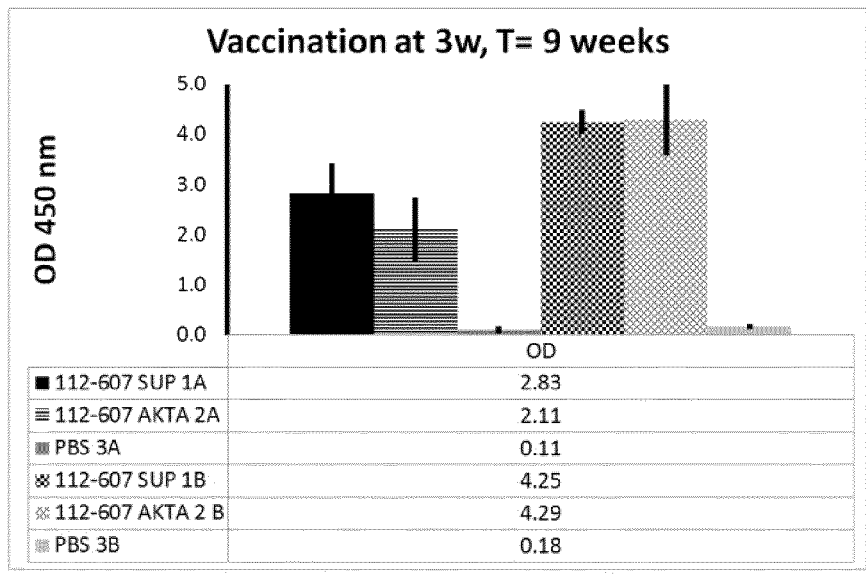
Figure 3F:
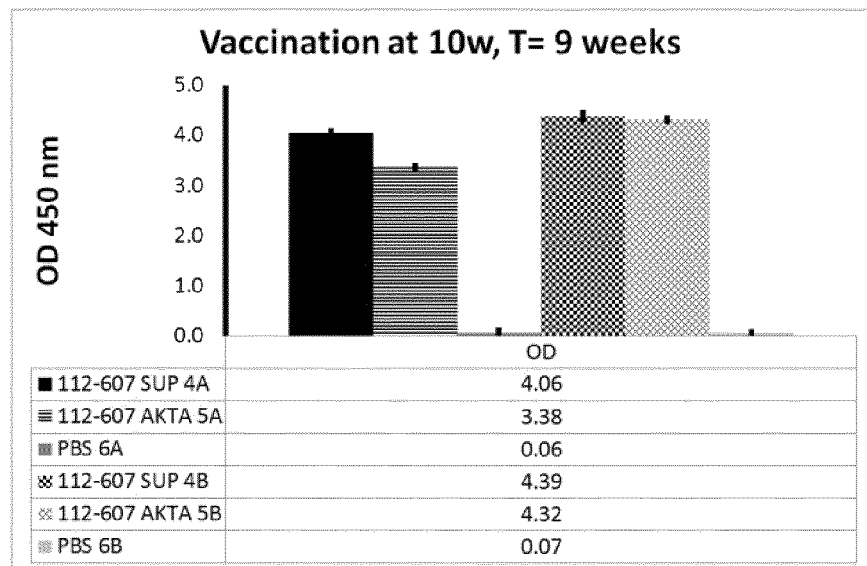

Even at 9 weeks after vaccination, the anti-HEV titer in MDA-positive piglets is only slightly lower than the anti-HEV titer in MDA-negative piglets (FIG. 3E, 3F).

The protein encoded by HEV ORF2 is the 72 kDa HEV capsid protein. A comparison between 11 different HEV ORF2 sequences shows that, although the sequence identity is not in all cases 100%, the length of the different ORF2 sequences is practically identical in all cases. (Meng, X-J. et al., Proc. Natl. Acad. Sci. USA. 94: 9860-9865 (1997).

HEV ORF2 starts from nucleotide (nt) 5147, extends 1,980 bases before ending at nt 7127, and codes for the major structural protein of 660 amino acids (88 kDa) that is expressed intracellular as well as on the cell surface. It is synthesized as a precursor and is processed through signal sequence cleavage into the mature protein, which is capable of self-association and glycosylation. Expression of the ORF2 coding sequence in Sf9 insect cells using the baculovirus system yields stable protein products with estimated molecular masses of 72 kDa and 59-62 kDa. The full length proteins from insect cells are insoluble, whereas truncated proteins comprising amino acids between position 112-607 and position 112-660 assemble into virus-like particles.

It is known that the minimal requirement for the formation of VLPs is the presence of the amino acids from position 125 to 601. (Surjit, M. et al. Journ. Virol. 78: 320-328 (2004), Li, T-C. et al., Journ. Virol. 79, 12999-13006 (2005)). However, the minimal neutralizing domain of HEV ORF2 has been mapped to amino acid residues 458-607 (Zhou, Y. H. et al., Vaccine 22: 2578-2585 (2004), Ahmad, I. et al., Virus Res. 161: 47-58 (201)).

For this reason, a vaccine according to the invention should at least comprise a HEV ORF2 protein fragment that includes the C-terminal amino acid residues from position 458-607.

At the same time that HEV ORF2 protein fragment should comprise the N-terminal amino acid residues from position 125-457 in order to be able to form VLPs.

Therefore the HEV ORF2 fragment in a vaccine for use according to the invention should at least comprise amino acid residues from position 125-607. However, at the same time the HEV ORF2 fragment should not comprise N-terminal additional amino acids of the region between 1 and 111, since such protein fragments would be less soluble, especially when made in an insect cell expression system.

Thus, preferably the minimal size of that fragment comprises amino acid residues from position 112-607, whereas at the same time the maximum size of that fragment comprises amino acid residues from position 112-660.

An example of the region between amino acid 112 and 607 of a HEV ORF2 protein sequence is presented in FIG. 5 (SEQ ID NO: 1).

The term "immunogenically effective amount" as used herein relates to the amount of HEV ORF2 protein fragment that is necessary to induce an immune response in piglets to the extent that it decreases the effects caused by infection with a wild-type HEV, when compared to the effects caused by infection with a wild-type HEV in non-immunized piglets.

It should be kept in mind that the main purpose of vaccination of young piglets against HEV is not so much the protection of the piglets against clinical symptoms, but the reduction of the amount of virus shed by infected piglets. This is due to the fact that on the one had the clinical signs in HEV-infected piglets are moderate to absent and on the other hand the final goal is to protect humans from becoming infected with HEV through contact with infected pig feces (i. a. the farmers) or infected pig meat. Therefore, the basic goal of the vaccination of piglets is to decrease the infection pressure in pig farms. For this reason it is clear to the skilled person that basically "an immunogenically effective amount" as used herein relates to the amount of HEV ORF2 protein fragment that is necessary to induce an immune response in piglets to protect against systemic infection. This protection against systemic infection in turn decreases the amount of virus shed by vaccinated piglets after they experience a HEV-infection, when compared to the amount of virus shed by non-vaccinated piglets after they experience a HEV-infection.

It is well within the capacity of the skilled person to determine whether a treatment is immunologically effective (i.e., whether an immunogenically effective amount of vaccine is administered), for instance by administering an experimental challenge infection to both vaccinated and non-vaccinated animals and next determining a target animal's serological parameters and by measuring the amount of virus shed, e.g. by taking rectal swabs, followed by comparison of these findings in the two challenge groups.

The amount of ORF2 protein fragment administered will depend on the route of administration, the presence of an adjuvant, the number of vaccinations and the moment of administration.

Merely as an example; depending on the adjuvant used, an amount of about 5 microgram HEV ORF2 protein/dose given as a single intramuscular vaccination is very well capable of inducing a protective immune response in three week old piglets having a high anti-HEV MDA-titer.

Preferably, a vaccine for use according to the present invention is characterised in that said vaccine comprises at least 10 microgram/dose of said protein fragment.

More preferably, a vaccine for use according to the present invention comprises at least 20 microgram/dose of said protein fragment.

Preferably an amount of about 15 microgram HEV ORF2 protein/dose, more preferably even 20, 30, 40, 50, 60, 70, 80, 90 or even 100 microgram/dose, in that order of preference, is administered.

Amounts of more than 100 microgram/dose, although feasible, would not add much to the level of protection, nor would they be attractive from a point of view of costs.

For the purpose of the present invention, a single vaccination is a vaccination that takes place only once (as opposed to a prime-boost vaccination regime).

For the purpose of the present invention, MDA-positive piglets are piglets that have a MDA antibody titer that has an optical density equal to or higher than $OD_{(450\ nm)}$ 0.25 when measured according to the ELISA method described in Example 4.

Thus, a first embodiment of the present invention relates to vaccines comprising an immunogenically effective amount of a protein fragment of Hepatitis E Virus Open Reading Frame 2 (HEV ORF2) spanning at least the region from amino acid 125 to amino acid 607 and at most the region from amino acid 112 to amino acid 660, and a pharmaceutically acceptable carrier, for use in the protection of MDA-positive piglets against HEV shedding.

The vaccine according to the invention can already be successfully used in piglets of 2-4 weeks of age. This is advantageous from an economical and animal welfare point of view since at this age piglets are often vaccinated with a vaccine against other pig diseases. The vaccines can thus be administered at or around the same moment.

Examples of pharmaceutically acceptable carriers that are suitable for use in a vaccine for use according to the invention are well-known in the art and comprise e.g. sterile water, saline, aqueous buffers such as PBS and the like.

In addition a vaccine for use according to the invention may comprise other additives such as adjuvants, stabilizers, anti-oxidants and others, as described below.

It is shown in FIG. 3 that a single vaccination with a composition according to the invention already provides a good protection against HEV in piglets, especially against shedding of progeny virus, so in principle no booster vaccination is required (see also Example 7, tables A and B).

However, even more surprisingly it was now found that if the vaccinated group with MDA-positive piglets and the vaccinated group with MDA-negative piglets received a second vaccination (a booster vaccination) several weeks after a first vaccination, the titer in both groups becomes even higher and levels off at practically the same titer in both groups. This shows that when piglets are both primed and boosted with fragments of the HEV ORF2 protein as described in the invention, they are even better protected against HEV shedding.

So in order to obtain an even higher and long lasting level of protection, a booster can be given. In principle, such a booster vaccine would be most efficacious when given somewhere between 3 and 15 weeks, preferably between 3 and 10 weeks after the first vaccination. More preferably, a booster would be given around five weeks after the first vaccination.

A booster vaccine would also comprise an amount of at least 10 microgram HEV ORF2 protein/dose. Preferably an amount of about 15 microgram HEV ORF2 protein/dose, more preferably even 20, 30, 40, 50, 60, 70, 80, 90 or even 100 microgram/dose, in that order of preference, is administered.

Thus, another embodiment relates to vaccines comprising at least 10 microgram/dose of a fragment of Hepatitis E Virus Open Reading Frame 2 (HEV ORF2) protein spanning at least the region from amino acid 125 to amino acid 607 and at most the region from amino acid 112 to amino acid 660, and a pharmaceutically acceptable carrier, for use as a booster vaccine for the protection of MDA-positive piglets that have been vaccinated with a priming vaccine against HEV shedding no longer than 15 weeks prior to being vaccinated with the boost vaccine.

In a more preferred form of this embodiment, the priming vaccine is a vaccine comprising at least 10 microgram/dose of a fragment of HEV ORF-2 protein spanning at least the region from amino acid 125 to amino acid 607 and at most the region from amino acid 112 to amino acid 660, and a pharmaceutically acceptable carrier.

The fragments of the HEV ORF2 protein as described in the invention can easily be obtained by expression of a DNA fragment encoding these fragments. Suitable expression systems well-known in the art are e.g. bacterial, baculovirus-based, yeast-based and eukaryotic cell-based expression systems. Such expression systems are extensively described in the art and they are commercially available. Kamili (vide supra) refers e.g. to examples of HEV ORF2 expression in both baculovirus-based and bacterial expression systems.

Baculovirus-based and bacterial expression systems would be the preferred systems in view of their ease of use and their relatively large yield. Of these two, the baculovirus-based expression system would be slightly more preferred.

The Examples section provides examples of the expression of fragments of HEV ORF2 protein spanning at least the region from amino acid 112 to amino acid 607 and at most the region from amino acid 112 to amino acid 660 in a baculovirus-based expression system.

A vaccine for use according to the invention preferably comprises an adjuvant. Conventional adjuvants, well-known in the art for use in pig vaccines are e.g. Freund's Incomplete adjuvant, vitamin E, non-ionic block polymers, muramyl dipeptides, Quill A®, mineral oil e.g. Bayol® or Markol®, vegetable oil, and Carbopol® (a homopolymer), or Diluvac® Forte.

Preferably, a vaccine for use according to the invention comprises a water-in-oil or oil-in-water adjuvant. Of these, the oil-in-water adjuvants are slightly preferred. The oil component in water-in-oil and oil-in-water adjuvants can be a mineral oil. However, there currently is a tendency to replace mineral oils by biodegradable oils such as e.g. squalane, squalene and tocopherol.

Thus, a vaccine for use according to the invention more preferably comprises an oil-in-water adjuvant.

The vaccine may also comprise a so-called "vehicle". A vehicle is a compound to which the polypeptide adheres, without being covalently bound to it. Often used vehicle compounds are e.g. aluminum hydroxide, -phosphate or -oxide, silica, Kaolin, and Bentonite.

In swine farming practice, swine are vaccinated against a number of pathogenic viruses or micro-organisms.

Therefore it is highly attractive, both for practical and economic reasons, to combine a vaccine according to the invention for pigs with e.g. an additional immunogen of a virus or micro-organism pathogenic to pigs, or genetic material (RNA/DNA) encoding an immunogen of said virus or micro-organism.

Thus, a preferred form of this embodiment relates to a vaccine for use according to the invention, wherein that vaccine comprises at least one other pig-pathogenic microorganism or pig-pathogenic virus and/or at least one other immunogenic component and/or genetic material encoding said other immunogenic component, of said pig-pathogenic microorganism or pig-pathogenic virus. An immunogen or immunogenic component is a component that induces an immune response in an animal. It can e.g. be a live attenuated or killed whole virus, bacterium or a parasite, or a protein or a sugar moiety of that virus, bacterium or parasite.

The most common pathogenic viruses and micro-organisms that are pathogenic for swine are *Brachyspira hyodysenteriae*, African Swine Fever virus, Nipah virus, Porcine Circovirus, Porcine Torque Teno virus, Pseudorabies virus, Porcine influenza virus, Porcine parvovirus, Porcine respiratory and Reproductive syndrome virus (PRRS), Porcine Epidemic Diarrhea virus (PEDV), Foot and Mouth disease virus, Transmissible gastro-enteritis virus, Rotavirus, *Escherichia coli*, *Erysipelo rhusiopathiae*, *Bordetella bronchiseptica*, *Salmonella cholerasuis*, *Haemophilus parasuis*, *Pasteurella multocida*, *Streptococcus suis*, *Mycoplasma hyopneumoniae* and *Actinobacillus pleuropneumoniae*.

Therefore, a more preferred form of this embodiment relates to a vaccine for use according to the invention, wherein the virus or micro-organism pathogenic to swine is selected from the group consisting of *Brachyspira hyodysenteriae*, African Swine Fever virus, Nipah virus, Porcine Circovirus, Porcine Torque Teno virus, Pseudorabies virus, Porcine influenza virus, Porcine parvovirus, Porcine respiratory and Reproductive syndrome virus (PRRS), Porcine Epidemic Diarrhea virus (PEDV), Foot and Mouth disease virus, Transmissible gastro-enteritis virus, Rotavirus, *Escherichia coli*, *Erysipelo rhusiopathiae*, *Bordetella bronchiseptica*, *Salmonella cholerasuis*, *Haemophilus parasuis*, *Pasteurella multocida*, *Streptococcus suis*, *Mycoplasma hyopneumoniae* and *Actinobacillus pleuropneumoniae*.

The preferred route of administration is the intramuscular or intradermal route. For intradermal administration, a needle-free device such as the IDAL® (MSD AH) would be the preferred device.

LEGEND TO THE FIGURES

FIG. 1: Protein expression HEV 112-607 in SF9 culture supernatant and SF9 cells at different harvesting time points after baculovirus infection:

A) Western Blot results after staining of the blot with αHIS antibody. After blotting of the SDS-PAGE gel, the membrane was stained for 1 hour with αHIS-MCA diluted at 1:500 in blocking buffer. Next, the membrane was washed with wash buffer and incubated for 1 hour with the secondary antibody GAM/IgG(H+L)/PO diluted at 1:1000 in blocking buffer. The membrane was washed again with wash buffer and incubated with Vector SG substrate diluted in 15 ml of 3M Sodium Acetate.

B) Instant blue protein staining on the SDS-PAGE gel. For instant blue staining, the SDS page gel was incubated for 2 hours in 10 ml of InstantBlue protein stain.

The Molecular weight marker with protein size in kDa is loaded in left lane. The size marker of 50 kDa is indicated. Expected size of HEV 112-607 is 55 kD.

Figure 2:
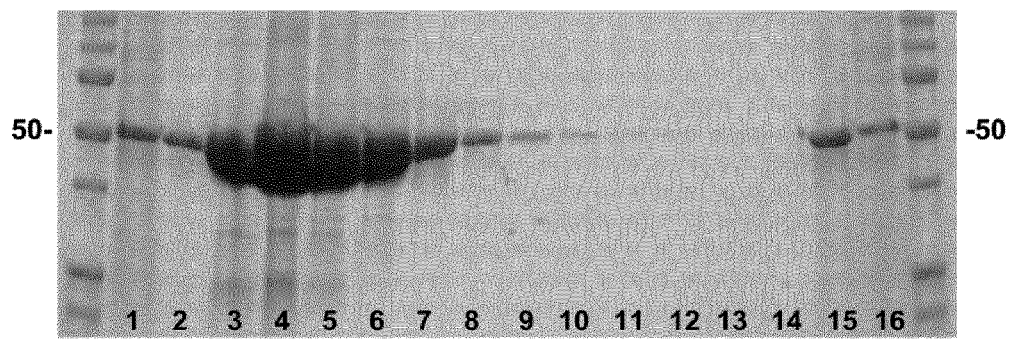

Loading of the samples is indicated with numbers:
1. harvest 3 days medium
2. harvest 3 days cell
3. harvest 4 days cell
4. harvest 4 days medium
5. harvest 5 days cell
6. harvest 5 days medium
7. harvest 6 days cell
8. harvest 6 days medium FIG. 2: Instant blue staining on SDS-PAGE gel of eluate fractions 1-14 of HEV 112-607 after AKTA Avant purification of protein harvested from culture supernatant. The eluate was collected in 2 ml fractions. Lanes 15, 16 correspond to the unbound and wash fractions, respectively. For instant blue staining, the SDS page gel was incubated for 2 hours in 10 ml of InstantBlue protein stain.

The molecular weight marker with protein size in kDa is loaded in the far left and right lanes. Expected size of HEV 112-607 is 55 kD.

Eluates 1 to 7 were pooled after purification.

FIG. 3: HEV specific antibodies measured at various time points in the vaccination study as determined in ELISA. Data are presented with error bars (Standard error of the mean, SEM)

A: 3-week-old piglets at the start of the experiment carried significant maternal antibody titers against HEV B: 10-week-old pigs at the start of the experiment carried reduced (maternal) antibody titers against HEV, which is in line with reduced maternal immunity at this age.

C: Vaccination with the 112-607 SUP and 112-607 AKTA vaccine resulted in seroconversion with specific antibodies to HEV ORF2 in the "3 week" age groups at T=4 weeks after vaccination. Maternal antibodies have not disappeared entirely.

D: Vaccination with the 112-607 SUP and 112-607 AKTA vaccine resulted in seroconversion with specific antibodies to HEV ORF2 in the "10 week" age groups at T=4 weeks after vaccination.

E: Vaccination with the 112-607 SUP and 112-607 AKTA vaccine resulted in seroconversion with specific antibodies to HEV ORF2 in the "3 week" age groups at T=9 weeks after vaccination (subgroups marked with A). A booster vaccination at 5 weeks after primo vaccination resulted in increased antibody titers at T=9 weeks after primo vaccination (subgroups marked with B) compared to primo vaccination only. Maternal antibodies have dropped below detection level.

F: Vaccination with the 112-607 SUP and 112-607 AKTA vaccine resulted in seroconversion with specific antibodies to HEV ORF2 in the "10 week" age groups at T=9 weeks after vaccination (subgroups marked with A). A booster vaccination at 5 weeks after primo vaccination resulted in increased antibody titers at T=9 weeks after primo vaccination (subgroups marked with B) compared to primo vaccination only.

FIG. 4: HEV specific antibodies measured at various time points in the vaccination-challenge experiment as determined in ELISA. Data are presented with error bars (Standard error of the mean, SEM)

FIG. 5: this figure shows the amino acid sequence of ORF 2 from a.a. sequence 112-607 (SEQ ID NO: 1).

FIG. 6: this figure shows the codon-optimised DNA sequence encoding the amino acid sequence of FIG. 5 (SEQ ID NO: 2).

EXAMPLES

Example 1

HEV ORF2 Expression in BAC to BAC Baculo Expression System

A domain of the ORF2 capsid protein of HEV genotype 3 [Swine hepatitis E virus, based on GenBank: AFJ06417.1), as depicted in FIG. 5 (SEQ ID NO: 1) was expressed in the BAC to BAC baculo expression system (Invitrogen). The protein was designed with a C-terminal HIS tag for purification.

The protein fragment expressed contains the core structural domain (amino acid 112-367) and the predicted neutralizing epitope (amino acid 456-607) but lacks the RNA binding domain of ORF2, the N-terminal 111 amino acids of the HEV ORF2.

The coding sequence of the HIS-tagged protein as depicted in FIG. 6 (SEQ ID NO: 2) was cloned into the pFastbac1 plasmid (Invitrogen). The coding sequence was designed with a flanking 5' BamHI restriction site, a start codon, the codon optimized nucleotide sequence of the protein, a HIS tag, a stop codon and a 3' EcoRI restriction site. This information was sent to Genscript (Piscataway, N.J., USA) where the nucleotide sequence was synthesized, digested with BamHI and EcoRI restriction enzymes and cloned into the pFastbac1 plasmid that was digested with the same restriction enzymes.

Subsequently, the protein was expressed using the Bac-to-Bac® Baculovirus Expression System according to the corresponding Instruction manual of Invitrogen Bac-to-Bac® Baculovirus Expression System. An efficient site-specific transposition system to generate baculovirus for high-level expression of recombinant proteins. Invitrogen. Catalog Numbers 10359-016, 10360-014, 10584-027, 10712-024. Document Part Number 10359, Publication Number MAN0000414).

Briefly, competent DH10Bac E. coli cells were transformed with plasmid DNA containing the nucleotide sequence as described above. Subsequently, the inserted sequence was transposed in the Bacmid sequence that is present in the DH10Bac cells. Next, bacteria were spread on agar plates containing antibiotics and IPTG. Selection was done by a white-blue screening since the white colonies contain the recombinant Bacmid. From a white colony a liquid culture was set up. Then, a miniprep isolation was performed to isolate the Bacmid DNA from the E. coli cells. SF9 insect cells were transfected (Cellfectin, Invitrogen) with this recombinant Bacmid DNA, resulting in formation of recombinant baculovirus particles. These particles were harvested and used to infect fresh monolayers of SF9 insect cells. The infection induces recombinant gene expression and the production of the HIS-tagged HEV-ORF2 protein 112-607.

To determine the time point of optimum protein yield, protein was harvested at different time points, 3, 4, 5 and 6 days after infection. In all these infection experiments the optimized MOI of 0.1 was used.

The recombinant protein that was expressed in SF9 cell culture medium or SF9 cells was collected. The cells were released from the culture flask by tapping and the cell suspension was centrifuged at 3.000×g for 10 minutes. Medium was harvested and stored until analysis at −70° C. Cell pellets were stored until analysis at −20° C. Both the supernatant and cell harvest were analyzed for protein expression. The pelleted cells were resuspended in PBS before analysis of protein expression. Samples of both harvests were run on a SDS-PAGE together with a protein prestained all blue marker (Biorad) and analyzed by Instant Blue staining (Expedeon) and Western Blot (αHIS-MCA).

For instant blue staining, the SDS page gel was incubated for 2 hours in 10 ml of InstantBlue protein stain.

For Western Blot, the Trans Blot Turbo Transfer Pack (Biorad) was used according to corresponding instruction manual. After blotting, the membranes were blocked for one hour with blocking buffer (1% skimmed milk in PBS 0.04 M, Polysorbate 20 0.05%). Subsequently, the membrane was stained for 1 hour with αHIS-MCA (MSD Animal or commercially available equivalent), diluted at 1:500 in blocking buffer. Next, the membrane was washed with wash buffer (PBS 0.04 M, Polysorbate 20 0.5%) and incubated for 1 hour with the secondary antibody GAM/IgG(H+L)/PO (Nordic) diluted at 1:1000 in blocking buffer. The membrane was washed again with wash buffer and incubated shortly with 3 drops of Vector SG substrate (Vector Laboratories) diluted in 15 ml of 3M Sodium Acetate.

Recombinant protein 112-607 was secreted in the culture medium as a soluble protein, but also present in the cell pellet (FIG. 1, A: Western blot, B: protein stain). The highest protein yield was achieved after 5 days of infection in culture medium. The culture medium containing the soluble protein was used for preparation of vaccine after inactivation of the baculovirus by gamma-irradiation=112-607 SUP (see: Example 3, vaccine preparation). From culture medium, also a purified subunit protein fraction was prepared. The HIS tagged protein was purified from the cell culture medium using the AKTA Avant protein purification system=112-607 AKTA (see Example 2, Purification method AKTA).

Example 2

Purification Method AKTA Avant Protein Purification System

HIS tagged protein 112-607 present in culture medium was purified using the AKTA Avant purification system (GE Healthcare, Germany).

The HIS tagged protein in the culture supernatant was purified on an AKTA Avant purification system (GE Healthcare, Germany) using a HiStrap FF column (GE Healthcare art. 17-5255-01 (5 ml). Prior to purification, the fraction was filtered on a 0.45 µM filter (Millipore).

The following program was used:

| Purification step | Buffer | CV | Flow speed |
|---|---|---|---|
| Equilibration | wash buffer AKTA non-denaturing | 5 | 1 ml/min |
| Sample application | Soluble fraction | | 1 ml/min |
| Wash | wash buffer non-denaturing | 4 | 1 ml/min |
| Gradient elution | wash buffer non-denaturing → elution buffer AKTA non-denaturing | 20 | 1 ml/min |
| 100% elution | elution buffer AKTA non-denaturing | 4 | 1 ml/min |
| Equilibration | wash buffer AKTA non-denaturing | 5 | 1 ml/min |

Wash buffer AKTA, non-denaturing: 300 mM KCl, 50 mM TRIS, 5 mM Immidazole
Elution buffer, non-denaturing: 300 mM KCl, 50 mM TRIS, 500 mM Immidazole The eluate was collected in 2 ml fractions and these were run on a SDS page gel followed by instant blue staining. The SDS page gel was incubated for 2 hours in 10 ml of InstantBlue protein stain (Expedeon) (FIG. 2). Eluates 1 to 7 were pooled after purification.

After purification, dialysis was performed on purified protein. The purified protein was loaded into a Spectra Por3 Dialysis membrane, MWCO 3.5 kD (Spectrum Labs) and this was placed into an external chamber with dialysis buffer (150 mM KCl+150 mM TRIS) of about 400 times the volume of the purified protein. The buffer was constantly stirred for 2 days at 4° C. and after 1 day the dialysis buffer was changed.

Example 3

Formulation of Vaccines

The X-solve formulation is an oil-in-water emulsion based on mineral oil combined with solubilized Vitamin E Acetate. Droplet size of the mineral oil based emulsion is about 0.5 µm and the droplet size of Solubilized Vitamin E Acetate is about 150 nm. Viscosity of the final vaccine is below 15 mPa·s.

The protein concentration of the antigen was determined as follows: The water-phase used for vaccine formulation was run on a SDS-PAGE together with a protein prestained all blue marker (Biorad) and a BSA standard with known protein concentration (25-50-100 µg/ml) and analyzed by Instant Blue staining (Expedeon). For instant blue staining, the SDS page gel was incubated for 2 hours in 10 ml of InstantBlue protein stain. The density of the signals was measured by GeneTools software from Syngene. The protein concentration of the 112-607 AKTA and 112-607 SUP were estimated based on linear regression on the BSA standard results.

112-607 AKTA: 40 µg/ml protein in final vaccine formulation
112-607 SUP: 40 µg/ml protein in final vaccine formulation Example 4

Determination of (Maternal) Antibody Levels in Serum

Individual blood samples (Vacuolette 8 ml Sep Clot Activator (Greiner-Bio One)) of pigs were collected. After clotting at room temperature and overnight at 4° C., serum was obtained from the blood samples. This was done by centrifugation of the tubes at 2,500×g for 25 minutes at 4° C. The serum samples for ELISA were heat inactivated for 30 minutes at +56° C. and finally stored at −20° C. or lower until use. The sera were tested for the presence of antibodies against HEV using the commercial test HEV ELISA 4.0 kit from MP Biomedicals, Santa Ana, Calif., USA. This was done according to the corresponding protocol of HEV ELISA 4.0 kit.

The cut-off value of the ELISA is OD (450 nm) 0.2+the average of the negative control samples (0.05). Samples with OD lower than 0.250 are considered HEV negative.

Example 5

Detection of HEV in Rectal Swabs, Bile and Serum

Individual blood samples (Vacuolette 8 ml Sep Clot Activator (Greiner-Bio One)) of pigs were collected. After clotting at room temperature and overnight at 4° C., serum was obtained from the blood samples. This was done by centrifugation of the tubes at 2,500×g for 25 minutes at 4° C. Serum samples for PCR were not heat inactivated and stored at −20° C. or lower until analysis.

Bile was taken from the gall bladder at necropsy using a syringe and stored at −20° C. or lower until analysis.

Rectal swabs were taken at different time points during the experiment. The swabs were placed in tubes containing 1 ml PBS and antibiotics. In the lab, tubes were vortexed and decanted in cryotubes. Samples were stored at −20° C. or lower until analysis.

The rectal swabs, bile and serum samples were tested for the presence of HEV RNA by q-RT-PCR.

RNA was extracted by the MagNA Pure 96 Instrument (Roche) using the external lysis protocol as described by the manufacturer. Briefly, 200 µl of undiluted sample was mixed with 250 µl external lysis buffer (Roche) and nucleic acids were extracted according to the related protocol.

For quantitative detection of HEV RNA in these samples, the QuantiTect Probe RT-PCR Kit (Qiagen) was used. A qPCR reaction consisted of 4.5 µl RNase free water, 12.5 µl QuantiTect Probe RT-PCR mastermix, 400 nm of the forward and reverse primer, 300 nm of the Probe, 0.75 µl QuantiTect Probe RT-mix (enzyme) and 5 µl RNA.

The following primers and probe were used:

```
Forward primer;
                              (SEQ ID NO: 3)
GGT GGT TTC TGG GGT GAC Reverse primer;
                              (SEQ ID NO: 4)
AGG GGT TGG TTG GAT GAA 6FAM TAMRA labeled probe;
                              (SEQ ID NO: 5)
TGA TTC TCA GCC CTT CGC
```

Reverse transcription was carried out at 50° C. for 30 min, followed by denaturation at 95° C. for 15 min. DNA was amplified immediately with 40 PCR cycles at 94° C. (15 s), 56° C. (30 s) and 76° C. (30 s). The reactions were run on the CFX96 real time system (Biorad) and the software analysis was done with CFX manager Version 3.1. Data are presented in copies/ml sample. Quantification was based on analysis of a set of standard samples containing $10^1$-$10^8$ HEV ORF2 copies/5 μl in each q-RT-PCR reaction on the CFX96.

Example 6

Vaccination Experiment

A total of 30 piglets of 3 weeks old that were seropositive for HEV maternal antibodies were used in this study. The piglets were randomly selected from different litters.

A total of 30 pigs of 10 weeks old were used in this study. The piglets were randomly selected. At the age of 10 weeks, maternal antibody levels to HEV have reduced compared to 2-week-old piglets (FIG. 3A, B).

The piglets of 3 weeks of age were assigned to 3 treatment groups of 10 piglets each (groups 1-2-3). Piglets of group 1 were vaccinated (IM vaccination, 1 ml, in the neck) at 3 weeks of age with HEV ORF2 vaccine 112-607 SUP formulated in X-Solve. Piglets of group 2 were vaccinated (IM vaccination, 1 ml, in the neck) at 3 weeks of age with HEV ORF2 vaccine 112-607 AKTA formulated in X-Solve. Piglets of group 3 were vaccinated (IM vaccination, 1 ml, in the neck) at 3 weeks of age with PBS.

The pigs of 10 weeks of age were assigned to 3 treatment groups of 10 piglets each (groups 4-5-6). Piglets of group 4 were vaccinated (IM vaccination, 1 ml, in the neck) at 10 weeks of age with HEV ORF2 vaccine 112-607 SUP formulated in X-Solve. Piglets of group 5 were vaccinated (IM vaccination, 1 ml, in the neck) at 10 weeks of age with HEV ORF2 vaccine 112-607 AKTA formulated in X-Solve. Piglets of group 6 were vaccinated (IM vaccination, 1 ml, in the neck) at 3 weeks of age with PBS.

Each group of 10 piglets was subdivided into A and B groups at 5 weeks post primo vaccination (8/15 weeks of age). 5 piglets received no booster vaccination (A subgroup), whereas the other 5 pigs received a booster vaccination identical to the primo vaccination (B subgroup).

Serum was collected prior to vaccination (3/10 weeks of age), at 7/14 weeks of age (4 weeks after vaccination) and 12/19 weeks of age (9 weeks after vaccination). Antibody levels to HEV were determined in serum as described in Example 4. Absence of replicating HEV was confirmed in all serum samples by q-RT-PCR analysis.

At 3 weeks of age, piglets had significant antibody titers against HEV, which had largely disappeared in pigs of 10 weeks of age (FIG. 3A, B). Vaccination with the 112-607 SUP vaccine (group 1) and 112-607 AKTA vaccine (group 2) resulted in seroconversion with specific antibodies to HEV ORF2 in both age groups at 4 (FIG. 3C, D) and 9 weeks after vaccination (FIG. 3E, F; subgroups A). A booster 5 weeks after primo vaccination resulted in increased antibody titers at 9 weeks after primo vaccination. (FIG. 3E, F; subgroups B)

Example 7

Vaccination-Challenge Experiment in Piglets

A total of 12 piglets of 3 weeks old that were seropositive for HEV maternal antibodies were used in this study. The piglets were randomly selected from different litters and housed together in one pen.

The piglets were assigned to 3 treatment groups of 4 piglets each (groups 1-2-3). Piglets of group 1 were vaccinated (IM vaccination, 1 ml, in the neck) at 3 weeks of age with HEV ORF2 vaccine 112-607 SUP formulated in X-Solve. Serum was collected prior to vaccination (3 weeks of age), at 7 weeks of age (4 weeks after vaccination) and prior to experimental challenge (11 weeks of age, 8 weeks after vaccination).

At 8 weeks after vaccination (11 weeks of age), the 4 pigs of group 2 were experimentally challenged with a liver homogenate of a HEV-positive animal from a Dutch farm. The challenge material was 10% liver homogenate in 50/50 (vol/vol) William's E medium/F-12 Ham medium. Challenge liver homogenate was applied via an intramuscular (IM) injection (2×2.5 ml, left and right neck) and oral dose of 15 ml applied using a syringe. For oral injection, the homogenate was centrifuged at 3,200×g for 1 hour at 4° C. and the supernatant was used for challenge. The material contained $2.12\times10^6$ HEV RNA copies/ml. For IM injection, this supernatant was centrifuged again at 10,000×g for 1 hour at 4° C., and subsequently filtered on a 0.22 μM filter (Millipore) and injected. This material contained $1.22\times10^6$ HEV RNA copies/ml. The HEV-positive material used contained a genotype 3i HEV which was determined based on RNA sequence analysis of the virus nucleotide sequence. The virus showed highest homology to Genbank accession number: KC618403.1. Pigs of group 3 served as contact sentinels.

Excretion of HEV via the feces after experimental challenge was monitored twice per week (12-17 weeks of age) by q-RT-PCR analysis of rectal swabs. Presence of virus in serum was monitored weekly (13-17 weeks of age) by q-RT-PCR analysis. Necropsies were performed at 17 weeks of age. Bile and blood were collected at the time of necropsy, with the exception of the group 2 animals. Presence of HEV virus was analyzed using q-RT-PCR (Example 5) in rectal swabs, bile and serum.

Antibody levels to HEV were determined in serum as described in Example 4. FIG. 4 shows the ELISA results. Vaccination of 3-week-old piglets induced a seroconversion with HEV specific antibodies in vaccinated animals which was detectable from 7 weeks of age onwards. Groups 2 and 3 showed decline in antibody titers due to disappearance of maternal antibodies prior to experimental challenge of group 2 at 11 weeks of age. Challenge of group 2 animals resulted in induction of HEV-specific antibodies in this group between 13 and 14 weeks of age, and also the Sentinel group 3 seroconverted as a consequence of infection with HEV due to direct contact with the experimentally challenged pigs. The sentinel group developed antibody titers between 15 and 16 weeks of age, with a delay of approximately 2 weeks compared to the experimental challenge group 2, which corresponds to the incubation time of the virus. The vaccinated group 1 reacted to exposure to HEV via experimentally challenged pigs (group 2) with an increase in HEV-specific antibody titers starting between week 14 and 15.

Successful experimental challenge of group 2, and infection of sentinel pigs in group 3 were confirmed by performing q-RT-PCR analyses on bile and serum of experimental animals (Table A). Three out of four experimentally challenged pigs, and four out of four sentinel pigs showed detectable levels of HEV in serum or bile. None of the vaccinated pig had detectable levels of HEV in serum or bile. Also rectal swabs were analyzed by q-RT-PCR analysis, which are shown in Table B.

The present experiment was set up to mimic field situations wherein HEV infects pigs during the finishing phase. Vaccination protected pigs from viremia in blood and bile (challenged animals, sentinel animals), which indicates that vaccinated pigs do not have a systemic infection with HEV. Furthermore, HEV vaccinated pigs react to exposure to the virus with increases serum antibody levels. Excretion of HEV in feces is reduced in vaccinated pigs compared to sentinel pigs in the same pen.

More specifically, what can be seen in Table B is that the vaccinated pigs, with respect to the sentinel pigs have a substantially reduced fecal shedding at weeks 13, 14 and 15 (factor 10-50 lower amount of HEV DNA material present in the feces). Around week 16 the shedding seems to be stabilized at a low level which is essentially the same for the vaccinated animals as well as the control animals. Since the vaccinated animals show no systemic infection with HEV at all (see Table A), this must be virus that is shed due to the piglets eating HEV infected feces. Apparently, the level of shedding arrived at after week 15 is due to eating infected feces, but not due to an actual infection of the animal. In short, when combining the data of Table A with those of Table B it is clear that with the present vaccine, an anti-HEV MDA-positive piglet can be protected against HEV fecal shedding, in particular against fecal shedding that is a result of an infection of the animal itself.

TABLE A q-RT-PCR analysis of serum and bile at various time points in the vaccination-challenge study (RNA copies/ml).

| Group | Treatment | Pig | week 17 BILE | week 11 SERUM | week 13 SERUM | week 14 SERUM | week 15 SERUM | week 16 SERUM | week 17 SERUM |
|---|---|---|---|---|---|---|---|---|---|
| 1 | Vaccinated | 1 | 0 | 0 | 0 | 0 | 0 | 0 | 0 |
| 1 | Vaccinated | 2 | 0 | 0 | 0 | 0 | 0 | 0 | 0 |
| 1 | Vaccinated | 3 | 0 | 0 | 0 | 0 | 0 | 0 | 0 |
| 1 | Vaccinated | 4 | 0 | 0 | 0 | 0 | 0 | 0 | 0 |
| | | average | 0 | 0 | 0 | 0 | 0 | 0 | 0 |
| 2 | Experimental challenge | 5 | NA | 0 | 1.5E+03 | 1.8E+03 | 0 | 0 | NA |
| 2 | Experimental challenge | 6 | NA | 0 | 1.3E+04 | 0 | 0 | 0 | NA |
| 2 | Experimental challenge | 7 | NA | 0 | 1.0E+03 | 3.7E+03 | 7.3E+04 | 1.2E+04 | NA |
| 2 | Experimental challenge | 8 | NA | 0 | 0 | 0 | 0 | 0 | NA |
| | | average | NA | 0 | 3.8E+03 | 1.4E+03 | 1.8E+04 | 2.9E+03 | NA |
| 3 | Sentinel | 9 | 6.5E+03 | 0 | 0 | 0 | 1.3E+03 | 0 | 0 |
| 3 | Sentinel | 10 | 0 | 0 | 0 | 0 | 6.2E+02 | 0 | 0 |
| 3 | Sentinel | 11 | 3.4E+03 | 0 | 0 | 0 | 0 | 0 | 0 |
| 3 | Sentinel | 12 | 8.8E+02 | 0 | 0 | 0 | 3.4E+02 | 0 | 0 |
| | | average | 2.7E+03 | 0 | 0 | 0 | 5.6E+02 | 0 | 0 |

NA: not analysed

TABLE B q-RT-PCR analysis of rectal swabs at various time points in the vaccination-challenge study (RNA copies/ml).

| | | | Age | | | | | | |
|---|---|---|---|---|---|---|---|---|---|
| | | | week 11 | week 12 | | week 13 | | week 14 | |
| Group | Treatment | Pig | challenge | 1 | 2 | 1 | 2 | 1 | 2 |
| 1 | Vaccinated | 1 | 0 | 0 | 0 | 0 | 0 | 0 | 3.1E+02 |
| 1 | Vaccinated | 2 | 0 | 0 | 0 | 0 | 0 | 2.1E+02 | 0 |
| 1 | Vaccinated | 3 | 0 | 0 | 0 | 0 | 0 | 2.4E+02 | 1.1E+03 |
| 1 | Vaccinated | 4 | 0 | 0 | 0 | 0 | 0 | 1.2E+02 | 4.6E+02 |
| | | average | 0 | 0 | 0 | 0 | 0 | 1.4E+02 | 4.6E+02 |
| 2 | Experimental challenge | 5 | 0 | 0 | 0 | 1.0E+04 | 2.6E+04 | 4.7E+05 | 1.4E+04 |
| 2 | Experimental challenge | 6 | 0 | 0 | 2.2E+02 | 1.2E+04 | 1.8E+05 | 6.5E+04 | 0 |
| 2 | Experimental challenge | 7 | 0 | 0 | 0 | 1.7E+04 | 4.9E+04 | 1.1E+06 | 2.4E+06 |
| 2 | Experimental challenge | 8 | 0 | 0 | 0 | 0 | 6.2E+03 | 2.6E+04 | 1.9E+04 |
| | | average | 0 | 0 | 5.6E+01 | 9.6E+03 | 6.5E+04 | 4.2E+05 | 6.0E+05 |
| 3 | Sentinel | 9 | 0 | 0 | 0 | 0 | 0 | 0 | 3.5E+02 |
| 3 | Sentinel | 10 | 0 | 0 | 0 | 0 | 5.0E+02 | 3.9E+02 | 3.8E+03 |
| 3 | Sentinel | 11 | 0 | 0 | 0 | 0 | 0 | 0 | 2.5E+03 |
| 3 | Sentinel | 12 | 0 | 0 | 0 | 0 | 0 | 7.1E+03 | 1.3E+04 |
| | | average | 0 | 0 | 0 | 0 | 1.2E+02 | 1.9E+03 | 5.0E+03 |

| | | | Age | | | | |
|---|---|---|---|---|---|---|---|
| | | | week 15 | | week 16 | | week 17 |
| Group | Treatment | Pig | 1 | 2 | 1 | 2 | 1 |
| 1 | Vaccinated | 1 | 1.5E+03 | 1.8E+02 | 0 | 0 | 3.9E+02 |
| 1 | Vaccinated | 2 | 7.5E+02 | 1.9E+02 | 1.3E+03 | 6.5E+02 | 3.8E+02 |
| 1 | Vaccinated | 3 | 1.4E+04 | 2.6E+02 | 0 | 0 | 1.6E+03 |
| 1 | Vaccinated | 4 | 4.2E+03 | 1.5E+02 | 6.9E+03 | 0 | 3.9E+02 |
| | | average | 5.1E+03 | 2.0E+02 | 2.0E+03 | 1.6E+02 | 6.8E+02 |

TABLE B-continued q-RT-PCR analysis of rectal swabs at various time points in the vaccination-challenge study (RNA copies/ml).

| | | | | | | | |
|---|---|---|---|---|---|---|---|
| 2 | Experimental challenge | 5 | 2.6E+04 | 1.6E+02 | 0 | 0 | 4.0E+02 |
| 2 | Experimental challenge | 6 | 4.1E+03 | 3.1E+02 | 5.2E+01 | 0 | 0 |
| 2 | Experimental challenge | 7 | 5.2E+06 | 9.8E+05 | 4.0E+04 | 5.0E+04 | 5.8E+05 |
| 2 | Experimental challenge | 8 | 1.3E+03 | 2.8E+03 | 3.9E+02 | 0 | 7.1E+02 |
| | | average | 1.3E+06 | 2.4E+05 | 1.0E+04 | 1.2E+04 | 1.5E+05 |
| 3 | Sentinel | 9 | 4.5E+02 | 1.8E+03 | 7.3E+02 | 0 | 9.2E+02 |
| 3 | Sentinel | 10 | 2.9E+03 | 3.5E+03 | 2.0E+03 | 0 | 0 |
| 3 | Sentinel | 11 | 4.1E+03 | 1.9E+04 | 2.0E+03 | 1.2E+02 | 0 |
| 3 | Sentinel | 12 | 2.4E+04 | 3.9E+03 | 1.4E+03 | 0 | 3.5E+02 |
| | | average | 7.8E+03 | 7.0E+03 | 1.5E+03 | 3.1E+01 | 3.2E+02 |

The invention claimed is:

1. A method for protecting anti-HEV MDA-positive piglets against HEV fecal shedding, the method comprising administering to the piglet a vaccine comprising an immunogenically effective amount of a protein fragment of Hepatitis E Virus Open Reading Frame 2 (HEV ORF2) spanning at least the region from amino acid 125 to amino acid 607 and at most the region from amino acid 112 to amino acid 660, and a pharmaceutically acceptable carrier.

2. A method according to claim 1, characterized in that said vaccine comprises at least 5 microgram/dose of said protein fragment.

3. A method according to claim 1, characterized in that said vaccine comprises at least 20 microgram/dose of said protein fragment.

4. A method according to claim 1, characterized in that said composition comprises an adjuvant.

5. A method according to claim 4, characterized in that said adjuvant is an oil-in-water adjuvant.

6. A method as described in claim 1, wherein the method additionally comprises a booster vaccination for the protection of the anti-HEV MDA-positive piglets that have been vaccinated with a priming vaccine against HEV shedding no longer than 15 weeks prior to being vaccinated with the boost vaccine.

7. A method according to claim 6, where said priming vaccine is a vaccine comprising at least 10 microgram/dose of the fragment of HEV ORF-2 protein spanning at least the region from amino acid 125 to amino acid 607 and at most the region from amino acid 112 to amino acid 660, and a pharmaceutically acceptable carrier.

8. A method according to claim 1, characterized in that said vaccine comprises at least one other pig-pathogenic microorganism or pig-pathogenic virus and/or at least one other immunogenic component and/or genetic material encoding said other immunogenic component, of said pig-pathogenic microorganism or pig-pathogenic virus.

9. A method according to claim 8, wherein the virus or microorganism pathogenic to pigs is selected from the group consisting of *Brachyspira hyodysenteriae*, African Swine Fever virus, Nipah virus, Porcine Circovirus, Porcine Torque Teno virus, Pseudorabies virus, Porcine influenza virus, Porcine parvovirus, Porcine respiratory and Reproductive syndrome virus (PRRS), Porcine Epidemic Diarrhea virus (PEDV), Foot and Mouth disease virus, Transmissible gastro-enteritis virus, Rotavirus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae*.

* * * * *

SEQUENCE LISTING

<160> NUMBER OF SEQ ID NOS: 5

<210> SEQ ID NO 1
<211> LENGTH: 503
<212> TYPE: PRT
<213> ORGANISM: Hepatitis E virus

<400> SEQUENCE: 1

```
Met Ala Val Ser Pro Ala Pro Asp Thr Ala Pro Val Pro Asp Val Asp
1               5                   10                  15

Ser Arg Gly Ala Ile Leu Arg Arg Gln Tyr Asn Leu Ser Thr Ser Pro
            20                  25                  30

Leu Thr Ser Ser Val Ala Ser Gly Thr Asn Leu Val Leu Tyr Ala Ala
        35                  40                  45

Pro Leu Asn Pro Leu Leu Pro Leu Gln Asp Gly Thr Asn Thr His Ile
    50                  55                  60

Met Ala Thr Glu Ala Ser Asn Tyr Ala Gln Tyr Arg Val Val Arg Ala
65                  70                  75                  80

Thr Ile Arg Tyr Arg Pro Leu Val Pro Asn Ala Val Gly Gly Tyr Ala
                85                  90                  95

Ile Ser Ile Ser Phe Trp Pro Gln Thr Thr Thr Thr Pro Thr Ser Val
            100                 105                 110

Asp Met Asn Ser Ile Thr Ser Thr Asp Val Arg Ile Leu Val Gln Pro
        115                 120                 125

Gly Ile Ala Ser Glu Leu Val Ile Pro Ser Glu Arg Leu His Tyr Arg
130                 135                 140

Asn Gln Gly Trp Arg Ser Val Glu Thr Ser Gly Val Ala Glu Glu Glu
145                 150                 155                 160

Ala Thr Ser Gly Ser Val Met Leu Cys Ile His Gly Ser Pro Val Asn
                165                 170                 175

Ser Tyr Thr Asn Thr Pro Tyr Thr Gly Ala Leu Gly Leu Leu Asp Phe
            180                 185                 190

Ala Leu Glu Leu Glu Phe Arg Asn Leu Thr Pro Gly Asn Thr Asn Thr
        195                 200                 205

Arg Val Ser Arg Tyr Thr Ser Thr Ala Arg His Arg Leu Arg Arg Gly
    210                 215                 220

Ala Asp Gly Thr Ala Glu Leu Thr Thr Thr Ala Ala Thr Arg Phe Met
225                 230                 235                 240

Lys Asp Leu His Phe Thr Gly Thr Asn Gly Val Gly Glu Val Gly Arg
                245                 250                 255

Gly Ile Ala Leu Thr Leu Phe Asn Leu Ala Asp Thr Leu Leu Gly Gly
            260                 265                 270
```

```
Leu Pro Thr Glu Leu Ile Ser Ser Ala Gly Gly Gln Leu Phe Tyr Ser
            275                 280                 285

Arg Pro Val Val Ser Ala Asn Gly Glu Pro Thr Val Lys Leu Tyr Thr
        290                 295                 300

Ser Val Glu Asn Ala Gln Gln Asp Lys Gly Ile Ala Ile Pro His Asp
305                 310                 315                 320

Ile Asp Leu Gly Asp Ser Arg Val Val Ile Gln Asp Tyr Asp Asn Gln
                325                 330                 335

His Glu Gln Asp Arg Pro Thr Pro Ser Pro Ala Pro Ser Arg Pro Phe
            340                 345                 350

Ser Val Leu Arg Ala Asn Asp Val Leu Trp Leu Ser Leu Thr Ala Ala
                355                 360                 365

Glu Tyr Asp Gln Thr Thr Tyr Gly Ser Ser Thr Asn Pro Met Tyr Val
    370                 375                 380

Ser Asp Thr Val Thr Phe Val Asn Val Ala Thr Gly Ala Gln Ala Val
385                 390                 395                 400

Ala Arg Ser Leu Asp Trp Ser Lys Val Thr Leu Asp Gly Arg Pro Leu
                405                 410                 415

Thr Thr Ile Gln Gln Tyr Ser Lys Thr Phe Tyr Val Leu Pro Leu Arg
            420                 425                 430

Gly Lys Leu Ser Phe Trp Glu Ala Gly Thr Thr Lys Ala Gly Tyr Pro
                435                 440                 445

Tyr Asn Tyr Asn Thr Thr Ala Ser Asp Gln Ile Leu Ile Glu Asn Ala
    450                 455                 460

Ala Gly His Arg Val Ala Ile Ser Thr Tyr Thr Thr Ser Leu Gly Ala
465                 470                 475                 480

Gly Pro Val Ser Val Ser Ala Val Gly Val Leu Ala Pro His Ser Ala
                485                 490                 495

Leu His His His His His His
            500

<210> SEQ ID NO 2
<211> LENGTH: 1512
<212> TYPE: DNA
<213> ORGANISM: Hepatitis E virus

<400> SEQUENCE: 2
atggctgttt ctcccgctcc cgacactgct cccgttcccg acgtggactc tcgtggtgcc      60
atcctgcgtc gtcaatacaa cctttctacc tcacccctga ctagctctgt tgctagcgga     120
accaacctgg tgctttacgc tgctcccctg aaccccctgc ttcccttca agacggcact     180 aacacccaca tcatggccac cgaggctagc aactacgccc ataccgtgt tgtgcgtgct     240 accatccgtt accgtcccct ggttcccaac gctgtgggcg ttacgctat cagcatctct     300 ttctggcccc aaaccactac cactcccacc agcgttgaca tgaactctat cacttcaacc     360
gacgttcgta tcctggtgca acccggcatc gctagcgaac tcgttatccc ctctgagcgt     420
ctgcactacc gtaaccaagg ctggcgtagc gttgaaacct ctggtgtggc cgaggaagag     480
gctacttcag aagcgttat gctgtgcatc catggctcac cgtgaacag ctacactaac     540 acccctaca ccggagctct gggtctcctg gacttcgctc tcgaactgga gttccgtaac     600 cttaccccg gcaacactaa cacccgtgtt tctcgttaca cttcaaccgc tcgtcaccgt     660
cttcgtcgtg gagccgacgg aaccgctgaa ctcaccacta ccgctgccac tcgtttcatg     720
aaagacctgc atttcactgg caccaacggc gttggcgaag tgggacgtgg catcgccctt     780
```

```
actctcttca accttgctga caccottctc ggaggcctcc ccactgaact gatctcaagc    840
gctggtggac aactcttcta ctcacgtccc gttgtgagcg ctaacggcga acccactgtt    900
aaactgtaca ccagcgtgga gaacgcccaa caagacaagg gtatcgctat cccccacgac    960
atcgaccttg gagactctcg tgttgtgatc caagactacg acaaccaaca tgagcaagac   1020
cgtcccaccc ccagccccgc tccctctcgt cccttctcag ttctgcgtgc taacgacgtg   1080
ctgtggctta gcctcaccgc tgccgaatac gaccaaacta cctacggctc ttcaactaac   1140
cccatgtacg ttagcgacac tgtgaccttc gttaacgtgg ctaccggcgc tcaagccgtt   1200
gctcgtagcc tcgactggtc taaggtgacc cttgacggtc gtcccctcac taccatccaa   1260
caatactcta agaccttcta cgttctgccc cttcgtggta aactgtcatt ctgggaggcc   1320
ggtactacca aggctggata cccctacaac tacaacacta ccgctagcga ccaaatcctt   1380
atcgaaaacg ctgccggcca tcgtgttgct atctctacct acactacctc actcggtgct   1440
ggacccgtga gcgtgtcagc cgttggcgtg cttgctcccc actctgccct ccatcatcat   1500
caccatcatt aa                                                      1512

<210> SEQ ID NO 3
<211> LENGTH: 18
<212> TYPE: DNA
<213> ORGANISM: Hepatitis E virus

<400> SEQUENCE: 3
ggtggtttct ggggtgac                                                  18

<210> SEQ ID NO 4
<211> LENGTH: 18
<212> TYPE: DNA
<213> ORGANISM: Hepatitis E virus

<400> SEQUENCE: 4
aggggttggt tggatgaa                                                  18

<210> SEQ ID NO 5
<211> LENGTH: 18
<212> TYPE: DNA
<213> ORGANISM: Hepatitis E virus

<400> SEQUENCE: 5
tgattctcag cccttcgc                                                  18
```